United States Patent
Kim et al.

(10) Patent No.: US 7,715,595 B2
(45) Date of Patent: May 11, 2010

(54) SYSTEM AND METHOD FOR IRIS IDENTIFICATION USING STEREOSCOPIC FACE RECOGNITION

(75) Inventors: Dae-Hoon Kim, Seoul (KR); Byung-Ho Choi, Seoul (KR); Seung-Min Paik, Seoul (KR)

(73) Assignee: Iritech, Inc., Herndon, VA (US)

( * ) Notice: Subject to any disclaimer, the term of this patent is extended or adjusted under 35 U.S.C. 154(b) by 6 days.

(21) Appl. No.: 12/253,864

(22) Filed: Oct. 17, 2008

(65) Prior Publication Data
US 2009/0041309 A1    Feb. 12, 2009

Related U.S. Application Data

(63) Continuation-in-part of application No. 10/501,569, filed on Jul. 13, 2004, now abandoned.

(51) Int. Cl.
G06K 9/00 (2006.01)
(52) U.S. Cl. .................. 382/117; 382/115; 382/118; 382/154; 382/255
(58) Field of Classification Search ............. 382/117, 382/154, 255
See application file for complete search history.

(56) References Cited

U.S. PATENT DOCUMENTS 5,625,408 A * 4/1997 Matsugu et al. ........... 348/42
5,729,619 A * 3/1998 Puma ..................... 382/115
2004/0150728 A1* 8/2004 Ogino ..................... 348/239
2005/0084179 A1* 4/2005 Hanna et al. ............. 382/294

FOREIGN PATENT DOCUMENTS

JP    10040386 A  *  2/1998

OTHER PUBLICATIONS

K. Hanna R Mandelbaum, D. Mishra, V. Paragano and L. Wixson, "A System for Non-Intrusive Human Iris Acquisition and Identification" IAPR Workshop on Machine Vision Applications, MVA '96, Nov. 12-14, 1996, Tokyo, Japan, pp. 200-203.*

* cited by examiner

*Primary Examiner*—Bhavesh M Mehta
*Assistant Examiner*—Eric Rush
(74) *Attorney, Agent, or Firm*—Intellectual Property Law Group LLP; Juneko Jackson; Otto O. Lee (57) ABSTRACT

Disclosed herein is a system and method for iris recognition including stereoscopic face recognition, which can recognize irises using a stereoscopic face recognition system in order to recognize an authenticatee. The system includes two or more face recognition cameras for photographing two or more face images of an authenticatee; a recognition system for receiving the face images photographed by the face recognition cameras from the face recognition cameras and creating stereoscopic face information on the basis of the face images; and one or more iris recognition cameras controlled by the recognition system to photograph focused irises of the authenticatee using the created stereoscopic face information.

16 Claims, 5 Drawing Sheets

SYSTEM AND METHOD FOR IRIS IDENTIFICATION USING STEREOSCOPIC FACE RECOGNITION

CROSS-REFERENCE TO RELATED APPLICATIONS

This application is a continuation-in-part of commonly owned U.S. patent application Ser. No. 10/501,569, filed on Jul. 13, 2004, which claims foreign priority under 35 U.S.C. §119 to Korean Patent Application no. 10-2002-0002632, filed in Korea on Jan. 16, 2002, the entire contents of which are hereby incorporated by reference.

BACKGROUND OF THE INVENTION

1. Field of the Invention

The present invention relates generally to a system and method for iris recognition using stereoscopic face recognition, which can recognize irises using a stereoscopic face image in order to recognize an authenticatee.

2. Related Art

As well known to those skilled in the art, in biometrics technologies parts of a human body are considered as recognition objects to recognize a person, iris, face, fingerprint, vein and the like recognition technologies are independently utilized.

However, certain biometrics technologies cannot be applied to certain persons. For example, the iris recognition technology cannot be applied to persons who are unable to open their eyes wide by nature or due to acquired diseases. The fingerprint recognition technology cannot be applied to persons who have worn fingerprints. Further, the face recognition technology cannot be applied to persons whose faces have been changed by plastic surgery, and so on. Accordingly, combined biometrics technologies, instead of the various independent biometrics technologies, have recently been developed to overcome these defects.

The overall recognition accuracy of the combined biometrics technologies is generally higher than the independent biometrics technologies applied individually.

For example, it is assumed that recognition accuracies of biometrics technologies A and B, different from each other, are 90% and 80%, respectively. If the biometrics technologies A and B are applied to one hundred persons, the ninety persons are recognized through the biometrics technology A in the case where the biometrics technology A is applied to the hundred persons, and eight persons are additionally recognized through the biometrics technology B in the case where the biometrics technology B is applied to the rest ten persons not recognized by the biometrics technology A. Accordingly, the overall recognition accuracy is 98%.

When the overall recognition accuracy is expressed as a formula, the overall recognition accuracy in the case where independent biometrics technologies having independent recognition accuracies with a % and b % are applied to persons one by one, is represented as the following Formula:

$$a+(100-a)*b/100(\%). \qquad \text{[Formula]}$$

The overall recognition accuracy is higher than the cases where the biometrics technologies A and B are independently applied.

Meanwhile, the conventional face recognition technology is utilized by taking a face image using a single camera, such that the face image cannot be analyzed in three dimensions. Accordingly, the face recognition technology has limitations, wherein the location of pupils can be detected but the distance information of the pupils from an iris camera cannot be obtained, both of which are required to capture the focused iris images.

Further, the conventional iris recognition technology has an added disadvantage in terms of the high cost auto-focusing camera of the iris recognition system. The conventional used, manually focused iris recognition camera system is inconvenient because it requires adjustment of the focal length and optical axis after aligning the pupils with the lens of the camera.

Moreover, the systems for iris recognition and face recognition are not operated as a module but are independently operated and so the systems are expensive and it is difficult to obtain a synergistic effect resulting from applying the location information of the pupils and the distance information of the pupils from a camera obtained in the process of the face recognition to iris recognition.

In a further improved system using a face recognition camera, one of the iris recognition cameras recognizes the locations of the pupils in the process of the face recognition, and then carries out the iris recognition. However, since a single face recognition camera is used, distances of the pupils from the iris recognition camera cannot be obtained, and a user must position his pupils at the optical axis of the camera so that an image is photographed in the vicinity of the focal point of the camera.

SUMMARY OF THE INVENTION

Accordingly, the present invention has been made keeping in mind the above problems occurring in the prior art, and an object of the present invention is to provide a system and method for iris recognition using stereoscopic face recognition, which can photograph irises of an authenticatee using a stereoscopic face image photographed by two or more cameras.

Another object of the present invention is to provide a method for individual identification using stereoscopic face recognition, which can identify an authenticatee using a stereoscopic face image photographed by two or more cameras without iris recognition of the authenticatee.

In order to accomplish the above object, the present invention provides a system for iris recognition using stereoscopic face recognition, including two or more face recognition cameras for photographing two or more face images of an authenticatee; a recognition system for receiving the face images photographed by the face recognition cameras from the face recognition cameras and creating stereoscopic face information on the basis of the face images, the information including detected location information of pupils of the authenticatee by extracting parts of the face from the face images, and a detected distance information between the pupils and the face recognition cameras by (i) obtaining a distance (dθ) between the two images on an image plane formed by the two face recognition cameras in a point (B) of an objective plane; (ii) obtaining a distance (l) between the objective plane and the face recognition cameras by dividing a value obtained by multiplying a distance (b) between the two face recognition cameras by a focal distance of the stereo cameras, by the distance (dθ) between the two images on the image plane formed by the two face recognition cameras in the point (B) of the objective plane; and moving the face recognition cameras by a distance obtained by subtracting the focal distance (f) of the two face recognition cameras from the distance between the objective plane and the face recognition camera in order to obtain a clear image; and one or more iris recognition cameras controlled by the recognition system to photograph irises of the authenticatee using the created stereoscopic face information.

In some embodiments, it is preferable that the created stereoscopic face information includes information on distance between pupils of the authenticatee and the face recognition cameras.

Additionally, it is preferable that the above-mentioned system for iris recognition using stereoscopic face recognition further includes an iris recognition camera driving system for moving the iris recognition cameras on the basis of the distance information to automatically focus the iris recognition cameras on the irises of the authenticatee, the iris recognition cameras being mounted on the driving system. Accordingly, the iris recognition system capture clear photographic images of irises by automatically adjusting the focuses of iris recognition cameras on the basis of the location and distance information of the pupils detected in the process of face recognition. Thus, instead of using a high cost camera with an autofocusing function, the manufacturing cost of the iris recognition system can be reduced.

Additionally, in some embodiments, it is preferable that the iris recognition cameras have lenses with 5 cm or more focal depth. When the authenticatee approaches the iris recognition system for his irises to be photographed, the location of the face can be recognized. Thereafter, if a message, for example, a voice message, which instructs the authenticatee to change the position of his face in upward or downward directions, left or right directions, or forward or backward directions, is transmitted to the authenticatee, the iris recognition system can easily photograph irises without using the iris recognition camera driving system. Cameras provided with telecentric lens systems can be employed as iris recognition cameras having lenses with 5 cm or more focal depth. Generally, in the case of telecentric lens systems, the focal depths of the lenses are approximately 10 cm to 15 cm.

Additionally, it is preferable that the iris recognition system further include a body provided with a protective glass which is opaque for visible light and transparent to infrared light in a front thereof, and the iris recognition cameras therein, a region with which the irises of the authenticatee are aligned being represented on the protective glass; and an infrared illumination device disposed around the iris recognition cameras and installed in the body together with the iris recognition cameras. That is, if the protective glass is attached to the front face of the body of the iris recognition system, the region is represented on the protective glass for the convenience of the authenticatee, the iris recognition system automatically performs iris recognition when the pupils of the authenticatee are aligned with the dotted region.

In order to accomplish the above object, the present invention provides a method for iris recognition using stereoscopic face recognition, including the steps of: photographing two or more face images of an authenticatee using two or more face recognition cameras to stereoscopically photograph a face of the authenticatee; calculating a location of the face of the authenticatee and a distance to pupils of the authenticatee by (i) obtaining a distance (dθ) between the two images on an image plane formed by the two face recognition cameras in a point (B) of an objective plane; (ii) obtaining a distance (l) between the objective plane and the face recognition cameras by dividing a value obtained by multiplying a distance (b) between the two face recognition cameras by a focal distance of the stereo cameras, by the distance (dθ) between the two images on the image plane formed by the two face recognition cameras in the point (B) of the objective plane; and photographing irises of the authenticatee using the calculated location of the face and the distance to the pupils.

In some embodiments, it is preferable that the step of photographing irises is performed by photographing irises after iris recognition cameras are moved on a basis of the calculated distance of the pupils.

Additionally, in some embodiments, it is preferable that the step of photographing irises includes the steps of: transmitting a message to the authenticatee so that the authenticatee can move to a certain location on a basis of the calculated distance to the pupils; and photographing irises if it is determined that the authenticatee has moved to the predetermined location.

Additionally, the method for using stereoscopic face recognition further includes the steps of: extracting boundaries of the irises and the pupils from the photographed irises of the authenticatee; and determining whether the authenticatee has taken a narcotic drug through a parameter analysis process for narcotic detection. Accordingly, by the method, it can be determined whether the authenticatee has taken a narcotic drug through iris recognition using stereoscopic face recognition.

In order to accomplish the other object, the present invention provides a method for individual identification using stereoscopic face recognition, including the steps of: photographing two or more face images of an authenticatee using two or more face recognition cameras to stereoscopically photograph a face of the authenticatee; extracting parts of a face of the authenticatee by a recognition software using the photographed face images; and determining whether stereoscopic face information created by the extracted parts of the face is the same as specific face information stored in a database.

In some embodiments, it is preferable that the specific face information stored in the database is created by the steps of photographing face images and extracting parts of a face of the authenticatee.

Additionally, in some embodiments, it is preferable that the specific face information stored in the database is generated by digitizing a picture of the authenticatee.

BRIEF DESCRIPTION OF THE DRAWINGS

In order to fully describe embodiments of the present invention, reference is made to the accompanying drawings. These drawings are not to be considered limitations in the scope of the invention, but are merely illustrative.

DETAILED DESCRIPTION OF SPECIFIC EMBODIMENTS

The description above and below and the drawings of the present document focus on one or more currently preferred embodiments of the present invention and also describe some exemplary optional features and/or alternative embodiments. The description and drawings are for the purpose of illustration and not limitation. Those of ordinary skill in the art would recognize variations, modifications, and alternatives. Such variations, modifications, and alternatives are also within the scope of the present invention. Section titles are terse and are for convenience only.

Figure 1:
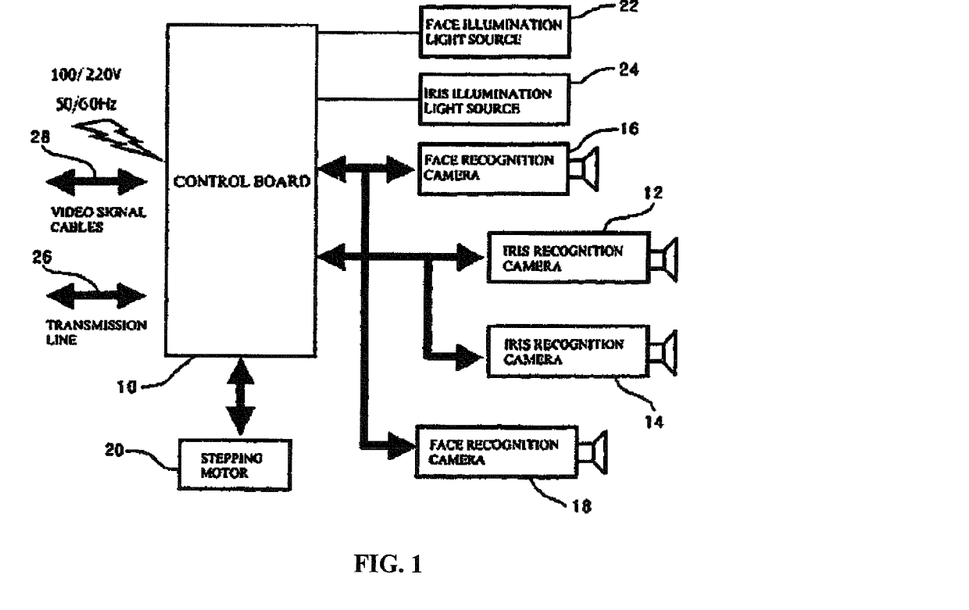
FIG. 1 is a control block diagram of a camera system for iris and face recognition in accordance with an embodiment of the present invention.

FIG. 1 is a control block diagram of the camera system for iris and face recognition in accordance with the preferred embodiment of the present invention. A control board 10 is connected to two iris recognition cameras 12 and 14 that photograph left and right irises of an authenticatee, respectively, two face recognition cameras 16 and 18 that photograph the face of the authenticatee from left and right sides respectively, and a stepping motor that adjusts the focal distances of the iris recognition cameras 12 and 14. Further, the control board 10 is connected to a face illumination light source 22 that illuminates the face of the authenticatee, an iris illumination light source 24 that illuminates the left and right irises of the authenticatee, respectively, a transmission line 26 that allows the operations of the cameras 12,14,16, and 18 to be controlled through serial communication with an application system, and video signal cables 28 that transmit iris and face image information obtained by the cameras 12,14,16, and 18 to the application system. The face illumination light source 22 is preferably implemented as a halogen lamp or infrared light emitting-diodes. The face illumination light source 22 is preferably implemented as infrared light emitting-diodes.

Face video signals corresponding to the face image information outputted from the two face recognition cameras 14 and 16 are transmitted to a recognition software of the application system, and parts of a face constituting the face, that is, the eyes, the nose, the mouth and so on, are extracted through image processing in the process of face recognition. Accordingly, the locations of pupils can be detected on the basis of the general characteristics of a human face. Additionally, the distance information of the pupils, that is, distances between the pupils and the face recognition cameras 16 and 18, is detected by analyzing the difference between left and right side images of the face. Accordingly, the moving distances of the iris recognition cameras 12 and 14 are calculated, and the calculated result is transmitted to the control board 10. The iris recognition cameras 12 and 14 are moved by driving the stepping motor 20 on the basis of the calculated result, so the focuses of the iris recognition cameras 12 and 14 are fixed on the irises and the irises are photographed. In this case, an interface that allows serial communication between the control board 10 and the application system through the transmission line 26 is implemented.

Figure 2:
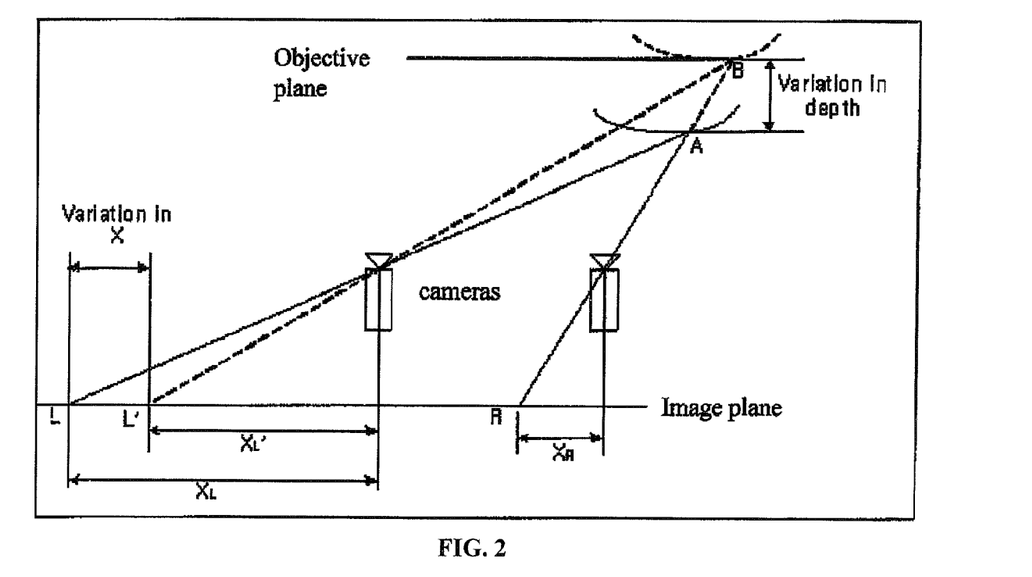
FIG. 2 is a perspective view depicting the calculation of a location of the face of the authenticatee and a distance from the face recognition cameras to the pupils of the authenticate in accordance with an embodiment of the present invention.

FIG. 2 is a detailed depiction of the calculation of the distance information of the pupils, that is, distances between the pupils and the face recognition cameras. As shown in FIG. 2, a left image acquired by the face recognition camera is denoted as the L-image, and a right image is denoted as the R-image. The L-image and R-image indicate the same point on the surface of an object, and the point is denoted as a corresponding point. As illustrated in FIG. 2, a spatial point A is indicated as a point R in the R-image and as a point L in the L-image. Thus, the points L and R become corresponding points. Similarly, points L' and R can be obtained from the point R and a spatial point B moved from the point A on a line extending from a right face recognition camera. When L(x,y) and R(x,y), respectively, denote the L-image and R-image, and N(x,y) is a function representing noise or a varied state caused by conditions such as light and a shadow, the relationship between the left image coordinates L(x,y) and the right image coordinates R(x,y) is represented according to Equation 1 below:

$$L(x,y)=R(x-D_x(x,y),y-D_y(x,y))+N(x,y)$$

Here, Dx and Dy are projected values and represent disparity of points (x,y) of the R-image on OX and OY axes. In FIG. 2, an objective plane OXY is perpendicular to the lens of the face recognition cameras and it is placed at a position having an appropriate distance l from the face recognition cameras. $z=\zeta(x,y)$ represents a field for evaluating the surface of the object, and z denotes a distance from the objective plane (z=0). A distance variation with respect to a specific point of the object is represented as $\Delta l=\zeta(x,y)$. Points on the objective plane are registered as basic disparity (d0). A variation in disparity values with respect to the points on the objective planes is represented as Δd. The objective plane includes a point B. In this case, the point B causes basic disparity (d0=L'−R). A point A is not placed on the objective plane and its disparity has a different value (dA=L−R). In general, a distance between characteristic points on the surface of the object is less than the distance between the object and the face recognition cameras. Thus, this relationship can be represented according to Equation 2 below.

$$\frac{d_0}{f}=\frac{b}{l},\ \frac{d_0+\Delta_d}{f}=\frac{b}{l-\Delta l},\ \Delta l \ll 1$$

Here, f denotes a focal distance of the two face recognition cameras, and b denotes a distance between the two face recognition cameras. A formula for evaluating the distance can be derived from Equation 3 below.

$$z(x,y)=\frac{l^2}{fb}(\rho((x_L,y_L),(x_R,y_R))-d_0) \qquad (3)$$

In the above Equation 3, a distance between the face recognition cameras and the object is obtained, and the face recognition cameras are moved by a stepping motor by a distance obtained by subtracting the focal distance from the distance between the face recognition cameras and the object, thereby acquiring a clear iris image of the object, obtained from the focal distance between two face recognition cameras.

In summary, in FIG. 2, the objective plane OXY is perpendicular to the lens of the two face recognition cameras and it is placed at the position having an appropriate distance l from the two face recognition cameras. Points on the objective plane are registered as basic disparity dθ. The variation in disparity values with respect to the points on the objective planes is represented as Δd. The objective plane includes the point B. In FIG. 2, the objective plane includes the point B. In this case, the point B causes basic disparity (dθ=L'−R).

In the above Equation 2, f denotes an invariable number of the focal distance between two face recognition cameras, and b denotes an invariable number of the distance between two face recognition cameras. When two images are used to calculate the basic disparity dθ, it is possible to calculate the distance l between the objective plane and the face recognition cameras. Therefore, a moving distance of the face recognition cameras between the object and the focal distance between two face recognition cameras is represented as $l$−f.

Although the number of the face recognition cameras is two in the embodiment of the present invention, the more stereoscopic face information can be obtained if a front face image can be photographed in the case of employing three or more face recognition cameras, so the accuracy of overall recognition can be increased.

Figure 3:
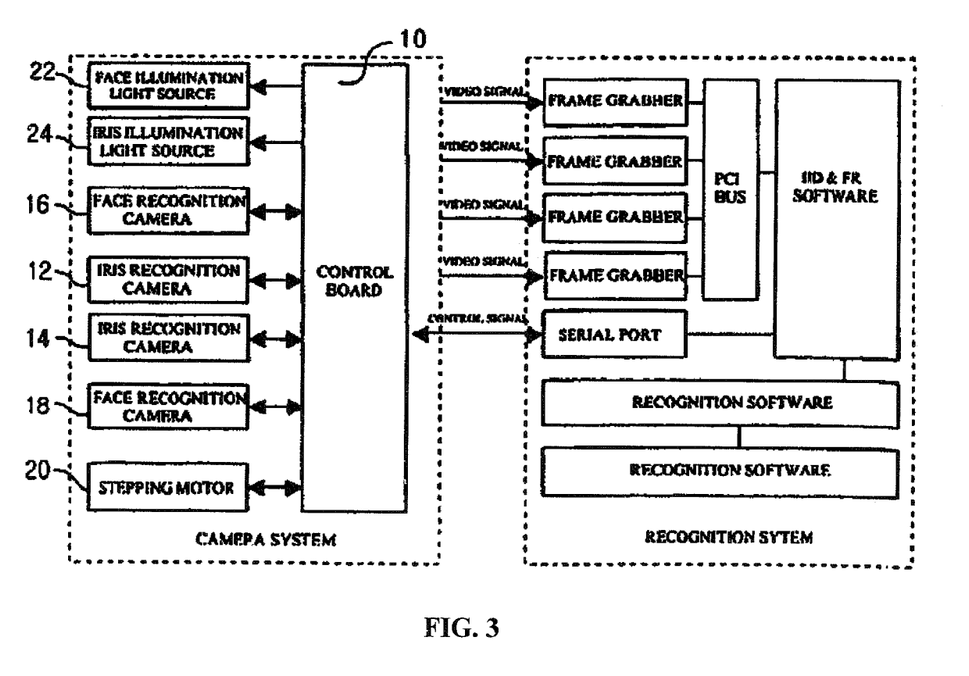
FIG. 3 is a block diagram illustrating an interface between the camera system and an application system in accordance with an embodiment of the present invention.

FIG. 3 is a block diagram illustrating an interface between the camera system and the application system in accordance with the present invention. The application system includes a plurality of frame grabbers, a serial port, a Peripheral Component Interconnect (PCI) bus, an Independent and Identically Distributed (IID) & False Rejection (FR) software, an application interface, and the recognition software. Video signals corresponding to the iris and face image information outputted from the iris recognition cameras 12 and 14 and the face recognition cameras 16 and 18 are transmitted to the recognition software through the frame grabbers installed in the application system, and the locations the pupils and the distances between the pupils and the face recognition cameras 16 and 18 are detected through the image processing and analysis. The detected results are transmitted to the control board 10, and the focal distances of the iris recognition cameras 12 and 14 are adjusted, so the iris recognition cameras 12 and 14 can clearly photograph the irises. In this case, the frame grabbers are apparatuses that convert analog image signals into digital signals processable in computers, and output the digital signals to another apparatus. That is, the frame grabbers are apparatuses that capture images and allow the captured images to be stored in a file form, and may be implemented as general frame grabbers in the present invention.

Figure 4:
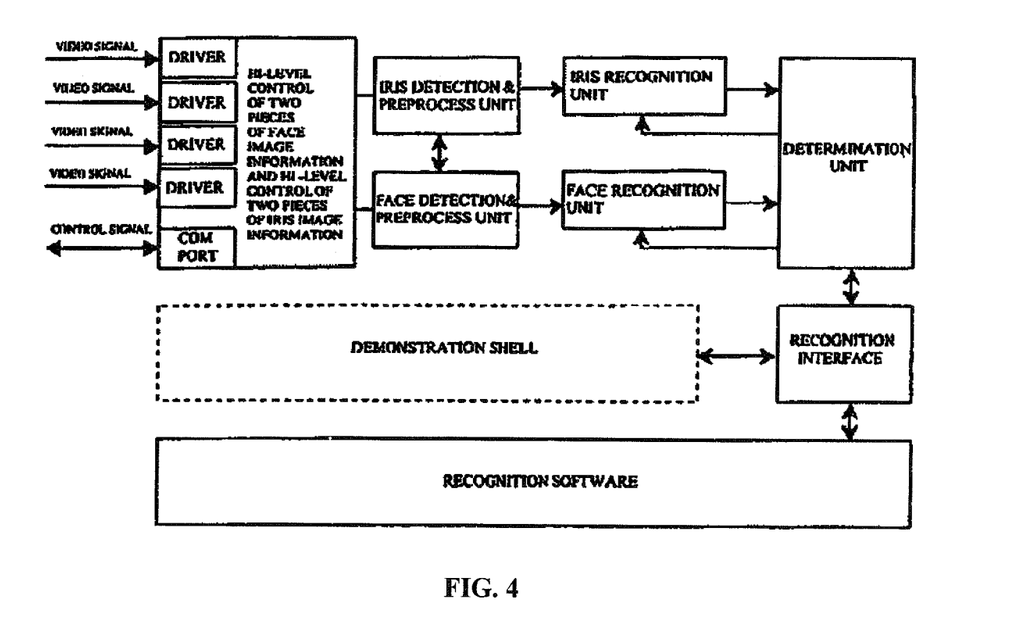
FIG. 4 is a block diagram illustrating the application system integrated to the camera system in accordance with an embodiment of the present invention.

FIG. 4 is a block diagram illustrating the application system integrated to the camera system in accordance with the present invention. The application system includes a plurality of drivers, a COMmunication (COM) port, an iris detection & preprocess unit, a face detection & preprocess unit, an iris recognition unit, a face recognition unit, a determination unit, the application interface, and the recognition software. Video signals corresponding to the iris and face image information outputted from the iris recognition cameras 12 and 14 and the face recognition cameras 16 and 18 are transmitted to the recognition software installed in the application system, and an authentication result which is obtained by the iris recognition and the face recognition for an authenticatee is transmitted to the application system through the interface.

Figure 5:
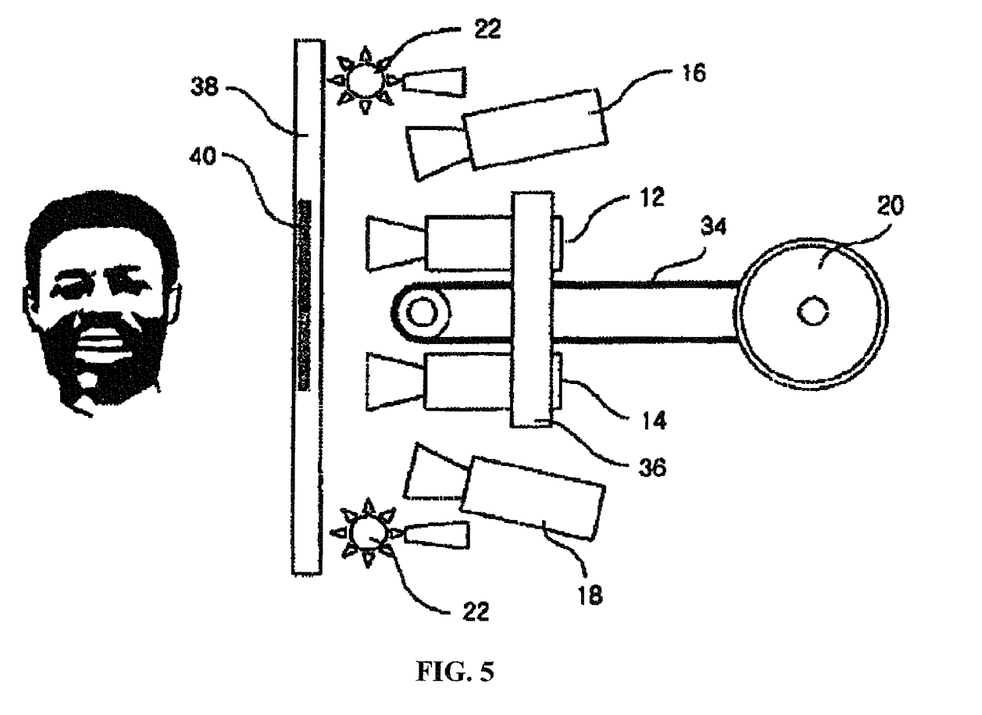
FIG. 5 is a schematic plan view of the inside configuration of the camera system of an embodiment of the present invention.
Figure 6:
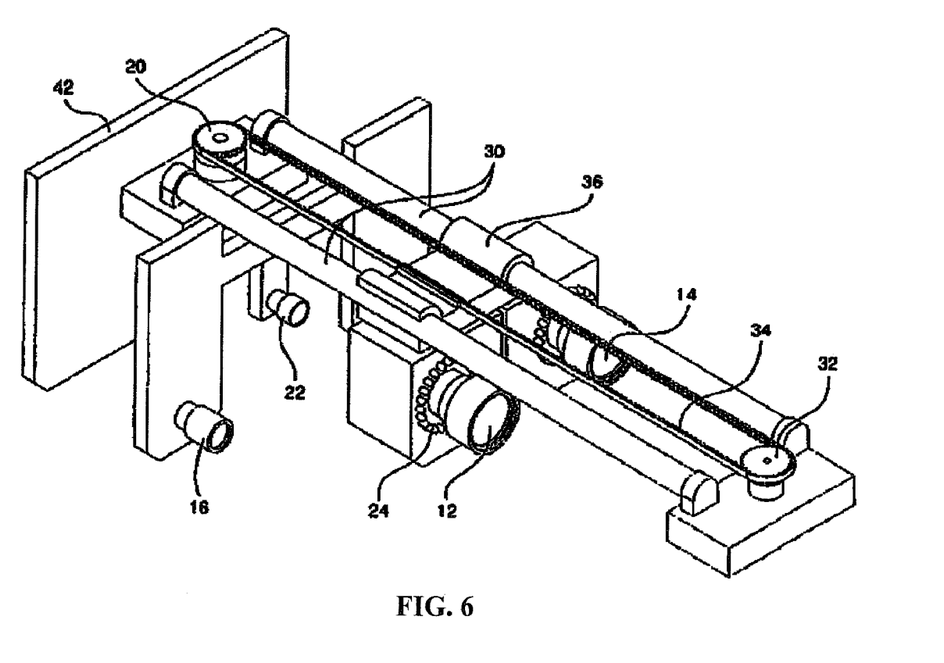
FIG. 6 is a perspective view of the inside configuration of the camera system of an embodiment of the present invention.

FIG. 5 is a schematic plan view of the inside configuration of the camera system of the present invention. FIG. 6 is a perspective view of the inside configuration of the camera system of the present invention, which is implemented as a single module.

The face recognition cameras 16 and 18 for photographing left and right sides of a face are disposed at lower left and right side portions of a body of the camera system. The iris recognition cameras 12 and 14 are disposed above and inside the face recognition cameras 16 and 18. The iris recognition cameras 12 and 14 are disposed so that a distance between them corresponds to the distance between the irises of a person. The iris recognition cameras 12 and 14 are fixedly attached to a supporting bracket 36, which is fitted around guide shafts 30, fixed to a toothed chain 34 wound around a stepping motor 20 and a roller 32, and moved by the stepping motor 20 to perform a focus adjusting function. Accordingly, the iris recognition cameras 12 and 14 carry out linear motion in the horizontal direction using the toothed chain 34 driven by the stepping motor 20, and move a short distance or a long distance from the irises of an authenticatee, so the focuses of the iris recognition cameras 12 and 14 are adjusted.

Although the stepping motor 20, the toothed chain 34, the roller 32, and the supporting bracket 36 constitute an iris recognition camera driving system in the preferred embodiment of the present invention, the elements of the driving system are not limited to the above elements and can be variously modified or adjusted by the person skilled in the art.

Meanwhile, when the irises of the authenticatee are not focused on the iris recognition cameras, a message is transmitted to the authenticatee so that the authenticatee can move to a predetermined location where the irises are focused, instead of directly moving the iris recognition cameras. If it is determined that the authenticatee has moved to the predetermined location, the irises are photographed. In this case, it is preferable that the focal depths of the lenses of the iris recognition cameras are more than 5 cm.

Meanwhile, the iris illumination light source 24 for illuminating the irises of the authenticatee is implemented as a plurality of the infrared light emitting diodes, which are disposed along the outer circumferences of the iris recognition cameras 12 and 14. Although an example in which the face illumination light source 22 is implemented as a halogen lamp is described in FIG. 6, it is obvious to those skilled in the art that the face illumination light source 22 may be implemented as the infrared light emitting diodes instead of the halogen lamp.

Further, a reflecting plate 42 is disposed behind the body, that is, behind the iris recognition cameras 12 and 14 and face recognition cameras 16 and 18.

The above-described camera system detects the locations of the pupils and the distances between the pupils and the face recognition cameras 16 and 18 in the process of the face recognition, drives the stepping motor 20 on the basis of the detected results, and moves the iris recognition cameras 12 and 14 disposed to the guide shafts 30 to locations in which the focuses of the iris recognition cameras 12 and 14 are clearly fixed on the irises. Thereafter, iris recognition is carried out. If the iris recognition is completed, the camera system controls the iris recognition cameras 12 and 14 to return to their original locations.

Accordingly, the camera system of the present invention implements a focus adjusting function for the irises using the face recognition software instead of using a high cost automatic focus camera.

Figure 7:
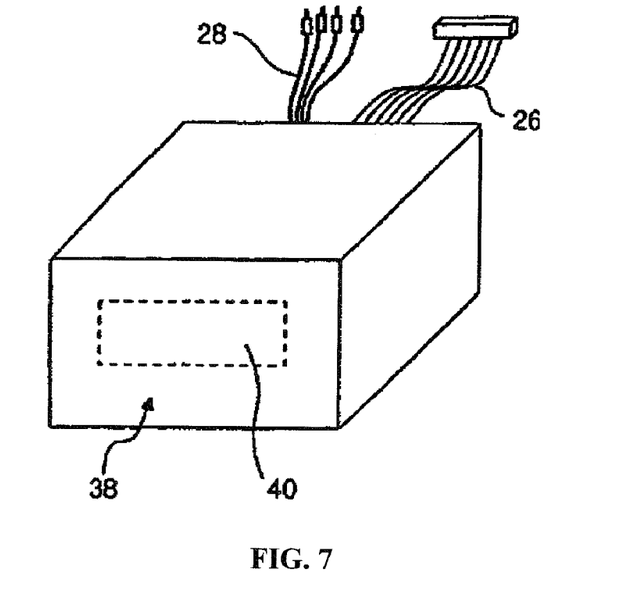
FIG. 7 is a perspective view of the external appearance of the camera system of an embodiment of the present invention.

FIG. 7 is a perspective view of the external appearance of the camera system of the present invention. Referring to FIG. 7, the camera system is implemented as a single module, and the front face of the camera system is formed by a protective glass 38. A region 40 represented by a dotted line is defined around the center part of the protective glass 38, which indicates the area with which the iris recognition cameras 12 and 14 are aligned. Accordingly, if the pupils of the authenticatee are aligned with the region 40 indicated by the dotted line, the face recognition and the iris recognition are automatically carried out. The protective glass 38 is constructed as a one-way mirror so that the inside of the camera system cannot be seen from the outside of the camera system. Accordingly, the iris and face images of the authenticatee are photographed using the protective glass 38 that transmits infrared rays and does not transmit visible rays, with illumination being controlled by infrared light. The transmitting of infrared rays means that 50% or more of infrared rays are transmitted through the protective glass 38, while the not transmitting of visible rays means that 50% or less of visible rays are transmitted through the protective glass 38.

This construction is used to increase user's convenience. That is, when the user aligns his pupils with the region 40 within the dotted line, the face recognition and the iris recognition are automatically carried out.

Hereinafter, a method of recognizing irises using the above-described camera system is described.

First, the face of the authenticatee is photographed from left and right sides using the face recognition cameras 16 and 18 so as to obtain stereoscopic face information.

Face video signals corresponding to face image information photographed by the face recognition cameras 16 and 18 are transmitted to the recognition software. Thereafter, the locations of the pupils are detected by extracting parts of the face constituting the face, that is, the eyes, the nose, the mouth and so on, through the image processing of the face recognition. Thereafter, the distances between the pupils and the face recognition cameras 16 and 18 are calculated by (i) obtaining a distance (dθ) between the two images on an image plane formed by the two face recognition cameras in a point (B) of an objective plane; (ii) obtaining a distance (l) between the objective plane and the face recognition cameras by dividing a value obtained by multiplying a distance (b) between the two face recognition cameras by a focal distance of the stereo cameras, by the distance (dθ) between the two images on the image plane formed by the two face recognition cameras in the point (B) of the objective plane, so as to adjust the focuses of the iris recognition cameras 12 and 14.

Thereafter, the camera system receives the distances between the pupils and the face recognition cameras 16 and 18 calculated as described above from the application system, moves the toothed chain 34 engaged with the stepping motor 20 on the basis of the distances, and adjusts the focuses of the iris recognition cameras 12 and 14 through the movement of the iris recognition cameras 12 and 14.

Thereafter, if the focus adjusting is completed, the iris recognition cameras 12 and 14 photograph the irises of the authenticatee, and output iris video signals corresponding to the photographed iris image information to the application system through the video signal cables 28, so iris recognition is carried out. If the iris recognition is completed by the application system, the camera system controls the iris recognition cameras 12 and 14 to return to their original locations by transmitting a control signal to the control board 10 through the transmission line 26, and prepares for a next photographing process.

Figure 8:
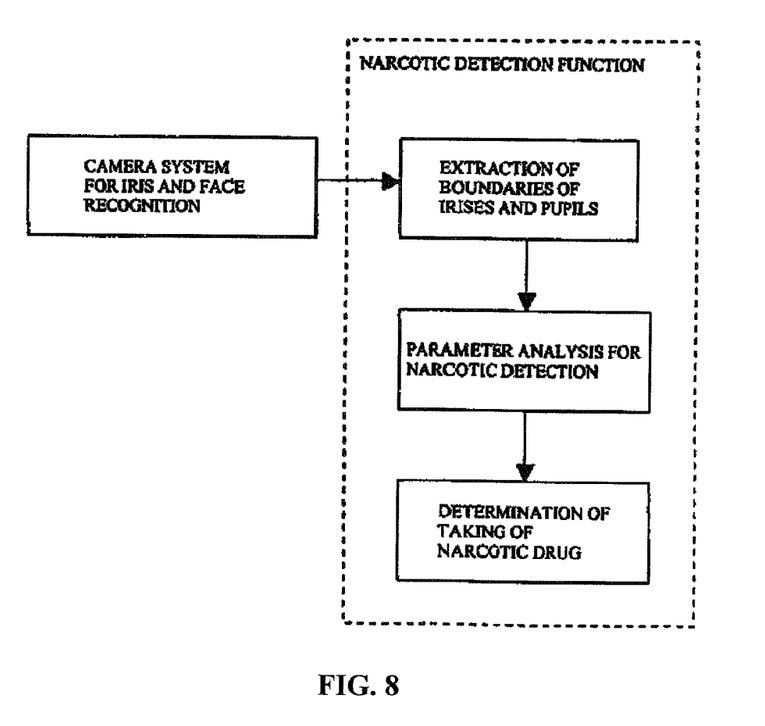
FIG. 8 is a flowchart illustrating a method for narcotic drug detection in accordance with another embodiment of the present invention.

FIG. 8 is a flowchart illustrating a method for narcotic detection in accordance with another embodiment of the present invention.

When narcotic detection is carried out, pupils are photographed by the iris recognition cameras 12 and 14 using the locations of the pupils and the distances between the pupils and the face recognition cameras 16 and 18 detected in the process of face recognition of the above-described camera system.

Thereafter, the boundaries of the irises and pupils are extracted from image information outputted from the iris recognition cameras 12 and 14, and it is finally determined whether an authenticatee has taken a narcotic drug through a parameter analysis process for the narcotic detection, as explained below.

The parameter analysis process for the narcotic detection is disclosed in Korean Pat. Unexamined Publication No. 2001-0097736 entitled "a method of detecting narcotic drugs using movement of pupils". The analysis is performed as follows. First, the movement of pupils in response to a physical stimulus applied one or more times, for example, light, sound, and heat, is photographed. Parameters, for example, initial pupil sizes, delay time of pupil contraction, response intensity of parasympathetic nerves, average response time of parasympathetic nerves, change rate of response time of parasympathetic nerve, minimum pupil sizes, duration of response of sympathetic nerves, change of response time of sympathetic nerve, and response intensity of the sympathetic nerve, are calculated from an obtained graph of the movement of pupils photographed by the iris recognition cameras 12 and 14. Thereafter, it is determined whether a narcotic drug has been taken according to each of conditions by comparing the calculated parameters with parameters for a normal person.

Figure 9:
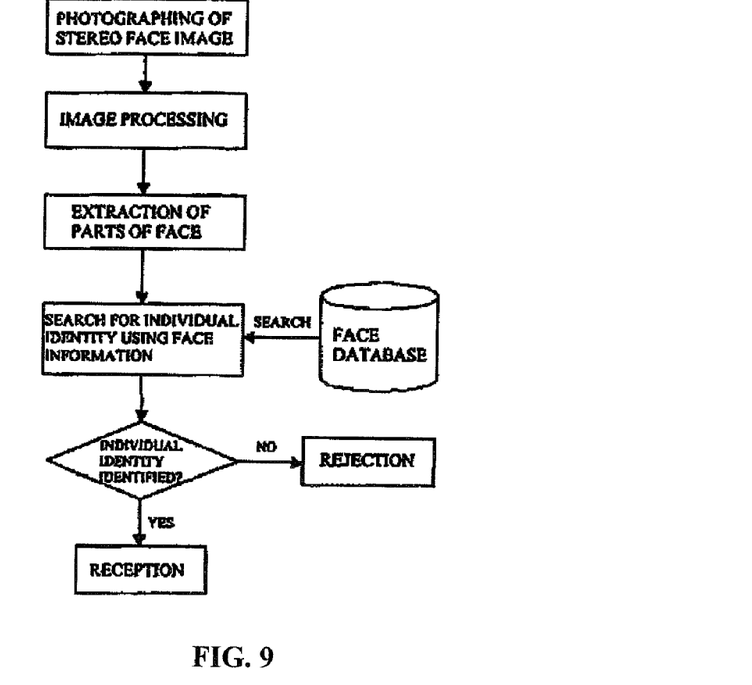
FIG. 9 is a flowchart illustrating a method for identifying persons in accordance with another embodiment of the present invention.
Figure 10:
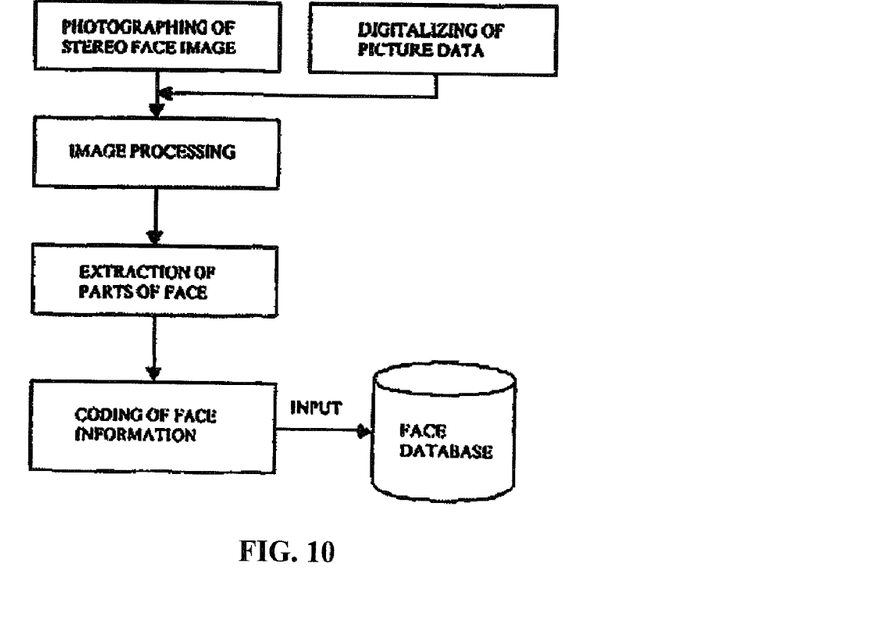
FIG. 10 is a flowchart illustrating a process for storing face information in a face information database illustrated in FIG. 9.

FIG. 9 is a flowchart illustrating a method for identifying persons in accordance with another embodiment of the present invention. FIG. 10 is a flowchart illustrating a process for storing face information in a face information database illustrated in FIG. 9.

Two or more face recognition cameras photograph the face images of an authenticatee. Thereafter, the parts (eyes, nose, mouth and so on) of the face of the authenticatee are extracted using the photographed face images through image processing in the recognition software. Thereafter, it is determined whether stereoscopic face information created by the extracted parts of the face is the same as specific face information stored in a face database. Through these processes, a person can be identified using stereoscopic face information in the case where data on his irises does not exist.

A face database for searching for individual identity stores data created by extracting the parts of a face through the image-processing of data photographed by the face recognition cameras, or data created by digitizing general pictures, such as, pictures on criminals, terrorists and so on.

INDUSTRIAL UTILITY

As described above, the system for iris recognition according to the present invention is a multi-biometrics camera, which is implemented as a single module, thereby being easily used in conjunction with the application system and increasing recognition accuracy.

Further, the present invention provides a method for individual identification using stereoscopic face recognition, which can identify an authenticatee using a stereoscopic face image photographed by two or more cameras without needing to perform iris recognition of the authenticatee.

Throughout the description and drawings, example embodiments are given with reference to specific configurations. It will be appreciated by those of ordinary skill in the art that the present invention can be embodied in other specific forms. Those of ordinary skill in the art would be able to practice such other embodiments without undue experimentation. The scope of the present invention, for the purpose of the present patent document, is not limited merely to the specific example embodiments or alternatives of the foregoing description.

What is claimed is:

1. A system for iris recognition using stereoscopic face recognition, comprising:
    two or more face recognition cameras for photographing two or more face images of an authenticatee;
    a recognition system for receiving the face images photographed by the face recognition cameras from the face recognition cameras and creating stereoscopic face information on the basis of the face images, the information including detected location information of pupils of the authenticatee by extracting parts of the face from the face images, and a detected distance information between the pupils and the face recognition cameras calculated by
        (i) obtaining a distance (dθ) between the two images on an image plane formed by the two face recognition cameras in a point (B) of an objective plane;
        (ii) obtaining a distance (l) between the objective plane and the face recognition cameras by dividing, a value obtained by multiplying a distance (b) between the two face recognition cameras by a focal distance of the stereo cameras, by the distance (dθ) between the two images on the image plane formed by the two face recognition cameras in the point (B) of the objective plane; and
        (iii) moving the face recognition cameras by a distance obtained by subtracting the focal distance (f) of the two face recognition cameras from the distance (l) between the objective plane and the face recognition cameras in order to obtain a clear image; and
    two or more iris recognition cameras controlled by the recognition system to photograph irises of the authenticatee using the created stereoscopic face information after adjusting a focal distance of the two or more iris recognition cameras based on the detected location and distance information.

2. The system for iris recognition using stereoscopic face recognition according to claim 1, further comprising an iris recognition camera driving system for moving the iris recognition cameras on the basis of the distance information to automatically focus the iris recognition cameras on the irises of the authenticatee, the iris recognition cameras being mounted on the driving system.

3. The system for iris recognition using stereoscopic face recognition according to claim 1, wherein the iris recognition cameras have lenses with 5 cm or more focal depth.

4. The system for iris recognition using stereoscopic face recognition according to claim 1, further comprising:
    a body provided with a protective glass which is opaque for visible light and transparent to infrared light in a front thereof, and the iris recognition cameras therein, a region with which the irises of the authenticatee are aligned being represented on the protective glass; and
    an infrared illumination device disposed around the iris recognition cameras and installed in the body together with the iris recognition cameras.

5. A method for iris recognition using stereoscopic face recognition, comprising the steps of:
    photographing two or more face images of an authenticatee using two or more face recognition cameras to stereoscopically photograph a face of an authenticatee;
    creating stereoscopic face information on the basis of the face images and detecting location information of pupils of the authenticatee by extracting parts of the face from the face images;
    calculating a distance between the stereoscopic face recognition cameras to pupils by
        (i) obtaining a distance (dθ) between the two images on an image plane formed by the two face recognition cameras in a point (B) of an objective plane;
        (ii) obtaining a distance (l) between the objective plane and the face recognition cameras; and
        (iii) moving the face recognition cameras by a distance obtained by subtracting the focal distance (f) of the two face recognition cameras from the distance (l) between the objective plane and the face recognition camera in order to obtain a clear image;
    adjusting two or more stereoscopic iris recognition cameras based on the calculated distance to pupils to adjust a focal distance of the iris recognition cameras; and
    photographing irises of the authenticatee with the two or more iris recognition cameras using the calculated location of the face and the distance to the pupils.

6. The method according to claim 5, wherein the distance (l) is obtained by dividing a value obtained by multiplying a distance (b) between the two face recognition cameras by a focal distance of the stereo cameras, by the distance (dθ) between the two images on the image plane formed by the two face recognition cameras in the point (B) of the objective plane.

7. The method according to claim 5, wherein the step of photographing irises comprises the steps of:
    transmitting a message to the authenticatee so that the authenticatee can move to a certain location on a basis of the calculated distance to the pupils, and position of the face; and
    photographing irises if it is determined that the authenticatee has moved to the predetermined location.

8. The method according to claim 5, further comprising the steps of:
    extracting boundaries of the irises and the pupils from the photographed irises of the authenticatee; and
    determining whether the authenticatee has taken a narcotic drug through a parameter analysis process for narcotic detection.

9. The method accordingly to claim 5, wherein the iris recognition cameras have lenses with 5 cm or more focal depth.

10. A system for iris recognition using stereoscopic face recognition, comprising:
    a camera system comprising: two or more face recognition cameras for photographing two or more face images of an authenticatee; two or more iris recognition cameras for photographing a left iris and a right iris of an authenticatee; a face illumination light source that illuminates a face of an authenticatee; an iris illumination light source that illuminates a left iris and a right iris of an authenticatee; a stepping motor for adjusting the iris recognition cameras; and a control board electrically connected to the face recognition cameras, the iris recognition cameras, the face illuminating light source, the iris illuminating light source and the stepping motor; and
    a recognition application system having recognition software configured for operation with the camera system through a transmission line;
    one or more video signal cables for transmitting iris and face image information obtained by the cameras to the recognition application system;

wherein the recognition application system receives the face images photographed by the face recognition cameras from the face recognition cameras and creates stereoscopic face information on the basis of the face images, the information including detected location information of pupils of the authenticatee by extracting parts of the face from the face images, and a detected distance information between the pupils and the face recognition cameras calculated by (i) obtaining a distance (dθ) between the two images on an image plane formed by the two face recognition cameras in a point (B) of an objective plane;

(ii) obtaining a distance (l) between the objective plane and the face recognition cameras by dividing a value obtained by multiplying a distance (b) between the two face recognition cameras by a focal distance of the stereo cameras, by the distance (dθ) between the two images on the image plane formed by the two face recognition cameras in the point (B) of the objective plane; and (iii) moving the face recognition cameras by a distance obtained by subtracting the focal distance (f) of the two face recognition cameras from the distance (l) between the objective plane and the face recognition camera in order to obtain a clear image; and wherein the stepping motor moves the iris recognition cameras on the basis of the calculated result, to focus the iris recognition cameras on the irises and photograph the irises of the authenticatee.

11. The system for iris recognition using stereoscopic face recognition according to claim 10, wherein the face illumination light source is a halogen lamp.

12. The system for iris recognition using stereoscopic face recognition according to claim 10, wherein the face illumination light source is an infrared light emitting-diodes.

13. The system for iris recognition using stereoscopic face recognition according to claim 10, wherein face recognition cameras for photographing a left side and a right side of a face are disposed at lower left and right side portions of a body of the camera system.

14. The system for iris recognition using stereoscopic face recognition according to claim 10, wherein the iris recognition cameras are disposed so that a distance between them corresponds to a distance between a left iris and a right iris of a person.

15. The system for iris recognition using stereoscopic face recognition according to claim 10, wherein the iris recognition cameras have lenses with 5 cm or more focal depth.

16. The system for iris recognition using stereoscopic face recognition according to claim 10, further comprising:

a body provided with a protective glass which is opaque for visible light and transparent to infrared light in a front thereof, and the iris recognition cameras therein, a region with which the irises of the authenticatee are aligned being represented on the protective glass; and an infrared illumination device disposed around the iris recognition cameras and installed in the body together with the iris recognition cameras.

* * * * *